United States Patent
Podgoreanu et al.

(10) Patent No.: US 8,105,781 B2
(45) Date of Patent: Jan. 31, 2012

(54) PREDICTORS OF LONG-TERM MORTALITY FOLLOWING CORONARY ARTERY BYPASS GRAFT SURGERY

(75) Inventors: Mihal V. Podgoreanu, Durham, NC (US); Joseph P. Mathew, Durham, NC (US); Robert L. Lobato, Durham, NC (US); Mark F. Newman, Durham, NC (US); Mark Stafford-Smith, Durham, NC (US); William D. White, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 12/251,287

(22) Filed: Oct. 14, 2008

(65) Prior Publication Data

US 2009/0155792 A1 Jun. 18, 2009

Related U.S. Application Data

(60) Provisional application No. 60/960,763, filed on Oct. 12, 2007.

(51) Int. Cl.
*C12Q 1/68* (2006.01)
*C12P 19/34* (2006.01)

(52) U.S. Cl. ........................ 435/6.11; 435/91.1; 435/91.2
(58) Field of Classification Search .................. None
See application file for complete search history.

(56) References Cited

U.S. PATENT DOCUMENTS

2008/0171332 A1* 7/2008 Sun et al. ........................ 435/6

OTHER PUBLICATIONS

Morgan, Thomas et al. Investigation of 89 candidate gene variants for effects on all cause mortality following acute coronary syndrome. 2008 BMC Medical Genetics. vol. 9:66 pp. 1-9.*
Juppner, H. Functional Properties of the PTH/PTHrP Receptor. 1995. Bone vol. 17 No. 2 Supplement pp. 39s-42s.*
Wu, Kenneth et al. Thrombomodulin Ala455Val Polymorphism and Risk of Coronary Heart Disease. Cicrulation 2001 vol. 103 pp. 1386-1389.*
Lobato et al, "Thrombomodulin Gene Variants Are Associated With Increased Mortality After Coronary Artery Bypass Surgery in Replicated Analyses", Circulation 124:S143-S148 (2011).

* cited by examiner

*Primary Examiner* — Amanda Shaw
(74) *Attorney, Agent, or Firm* — Nixon & Vanderhye P.C.

(57) ABSTRACT

The present invention relates, in general, to perioperative depression and, in particular, to methods of identifying individuals at risk of perioperative depression.

2 Claims, 9 Drawing Sheets

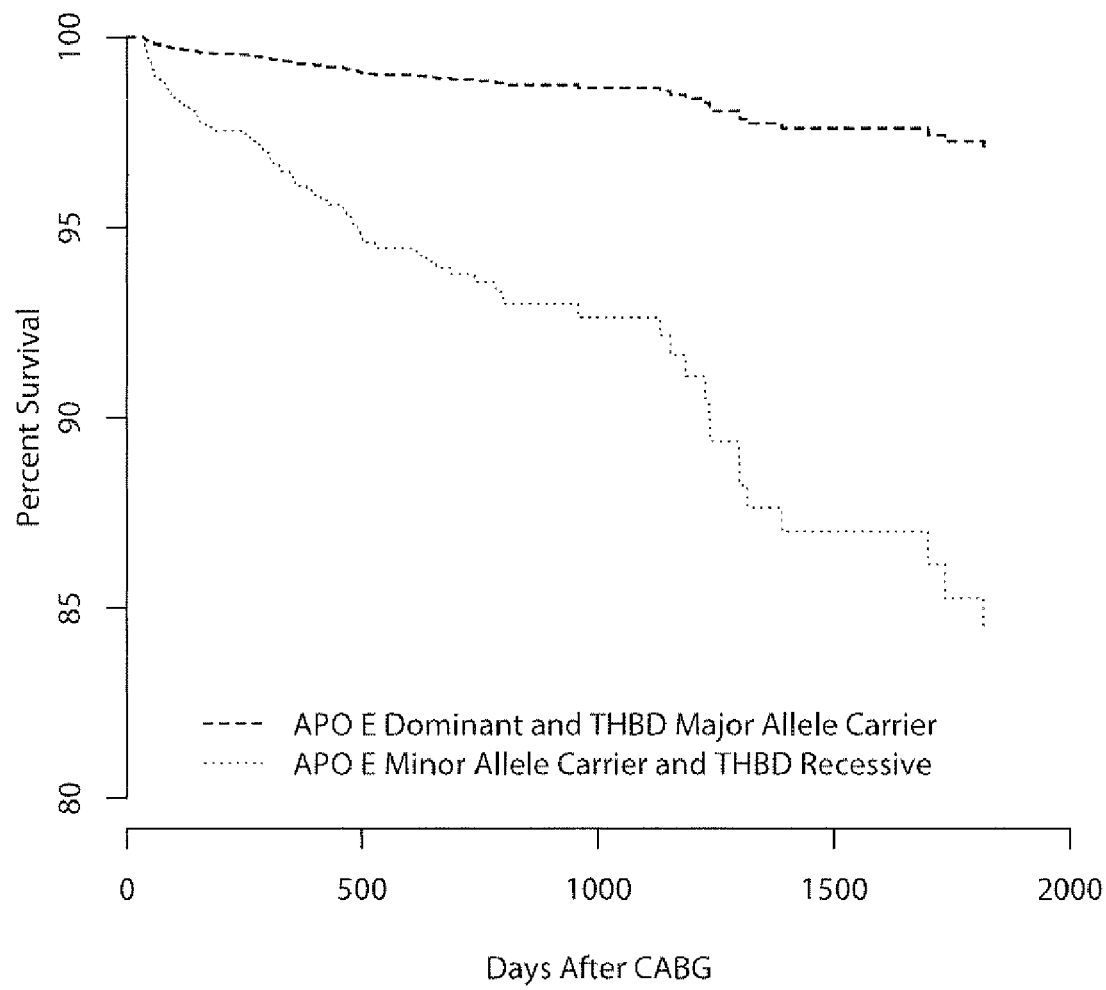
Figure 1 : Cox Proportional Hazard Model of EruoSCORE-adjusted Survival by Genotype

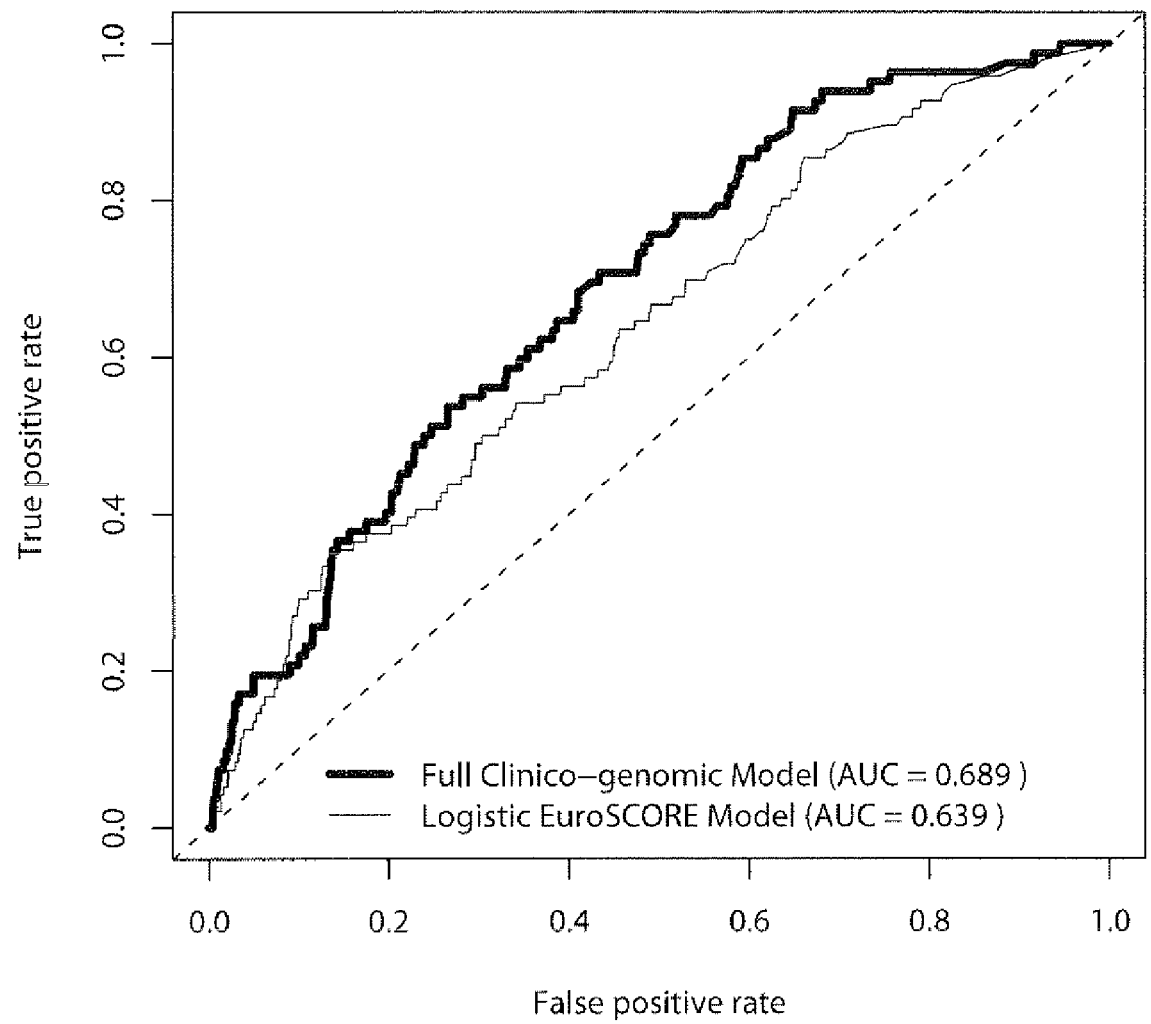
Figure 2: ROC Analysis of EruoSCORE and Clinico-genetic Models

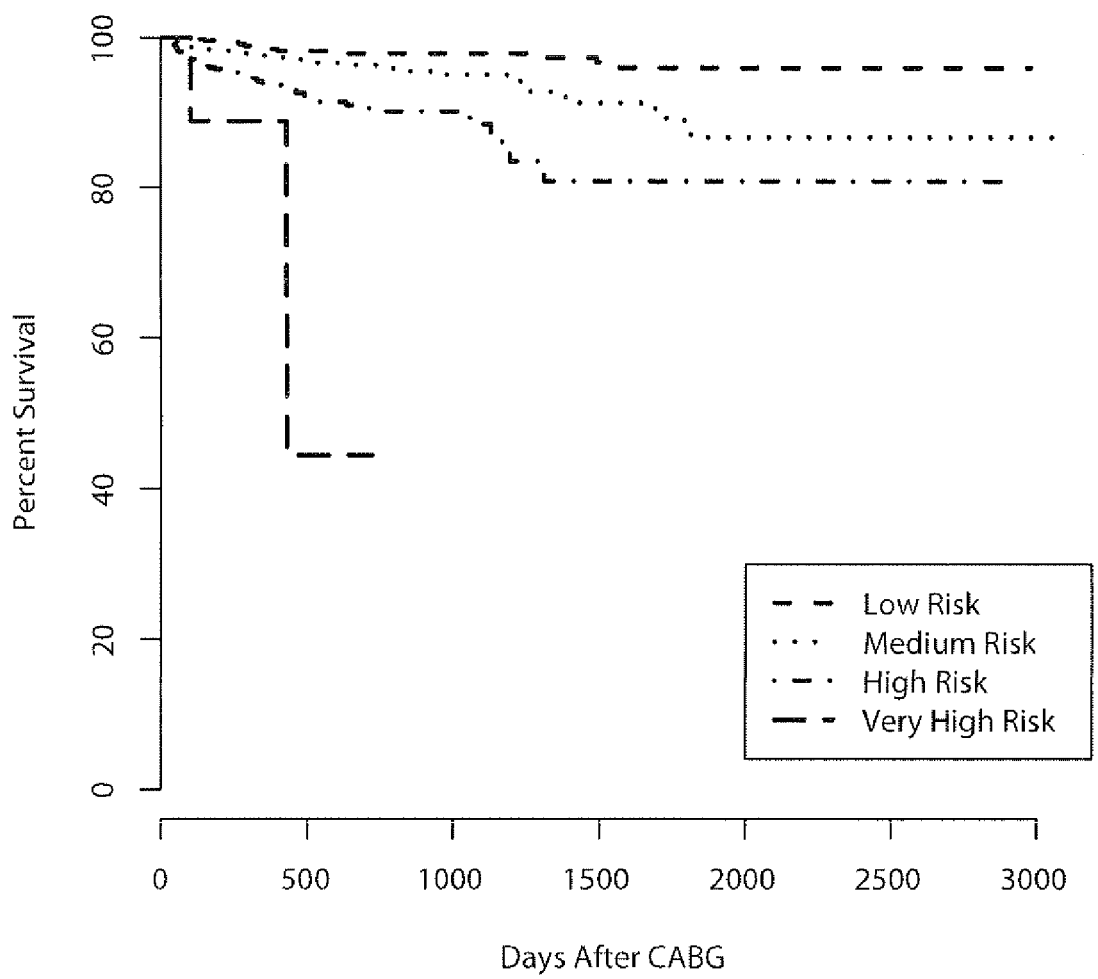
Figure 3: Baseline Kaplan-Meier Survival by EuroSCORE Category

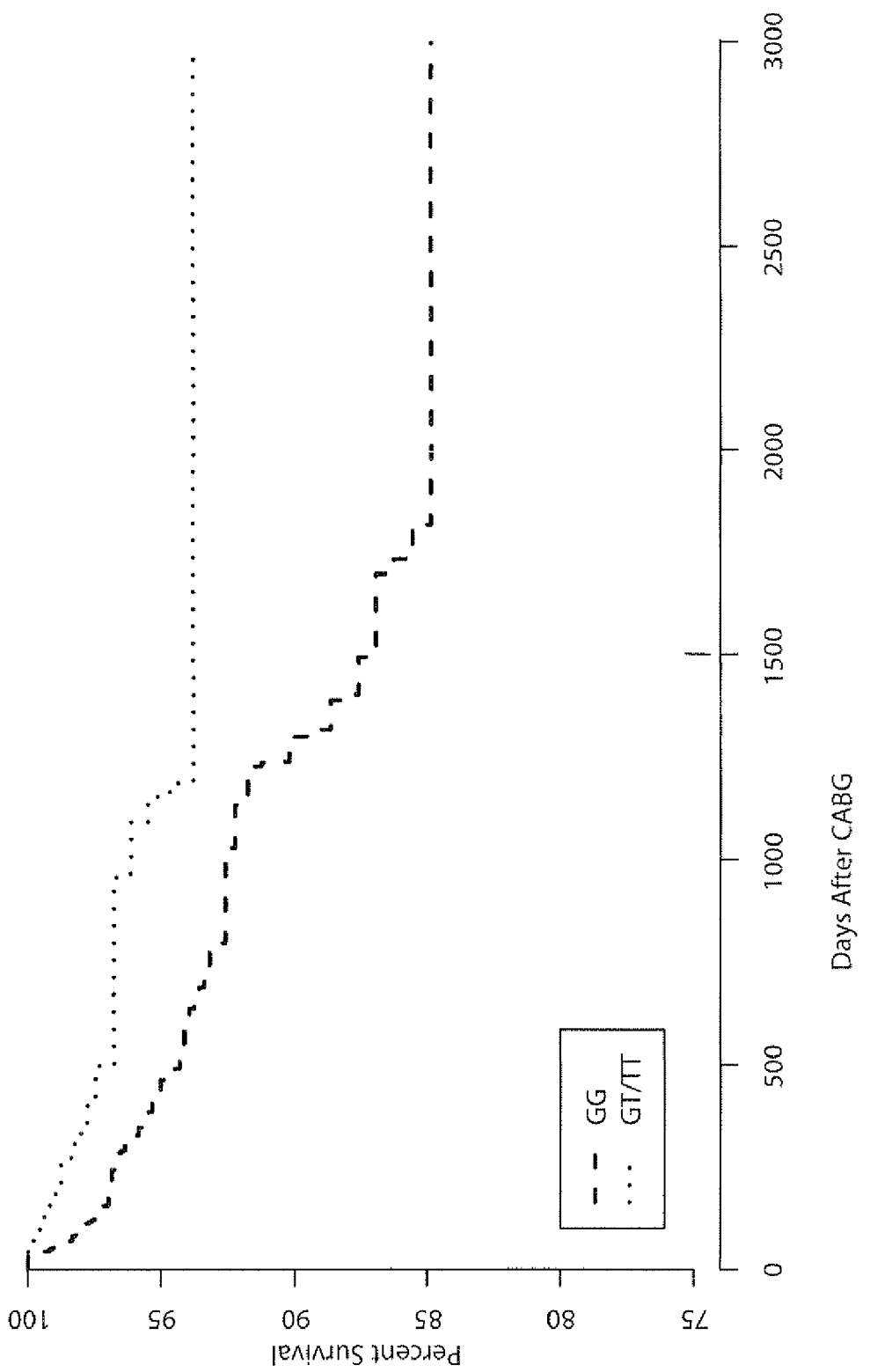

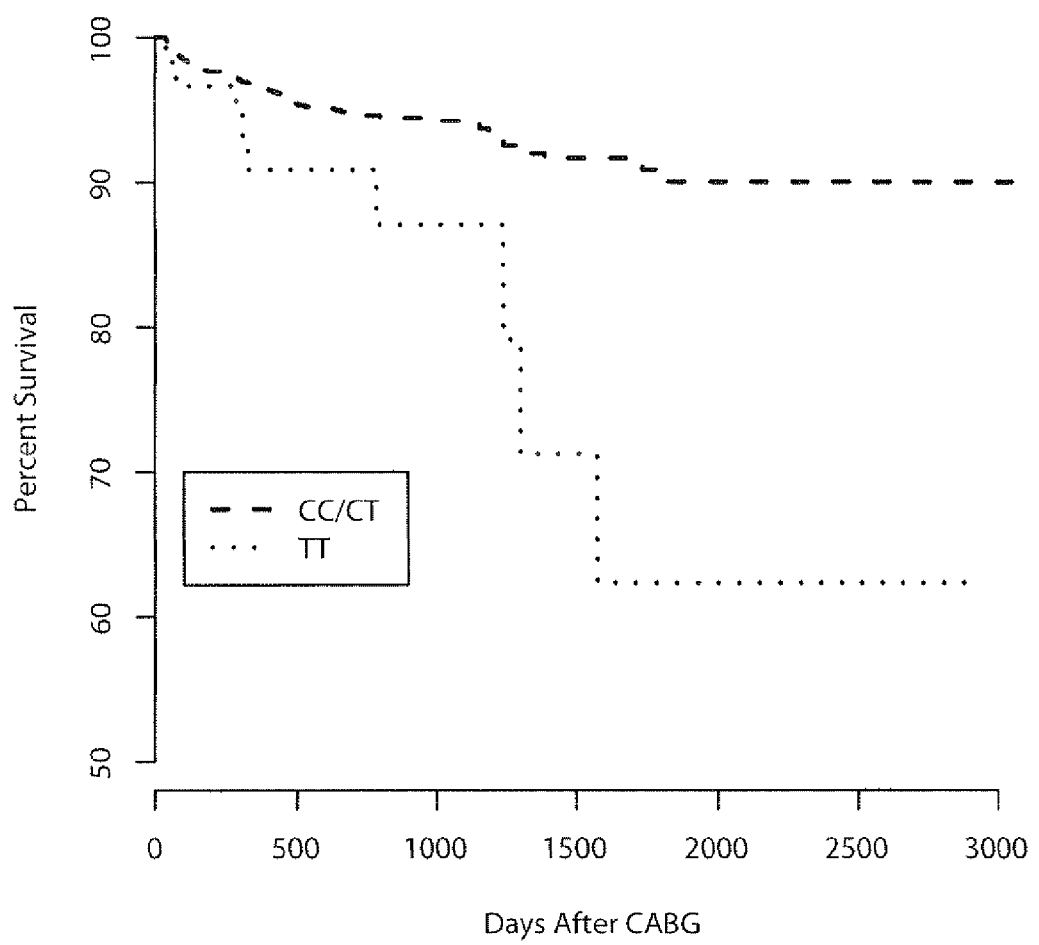
Figure 5: Kaplan-Meier Survival for RS1042579 Recessive Genotype Model

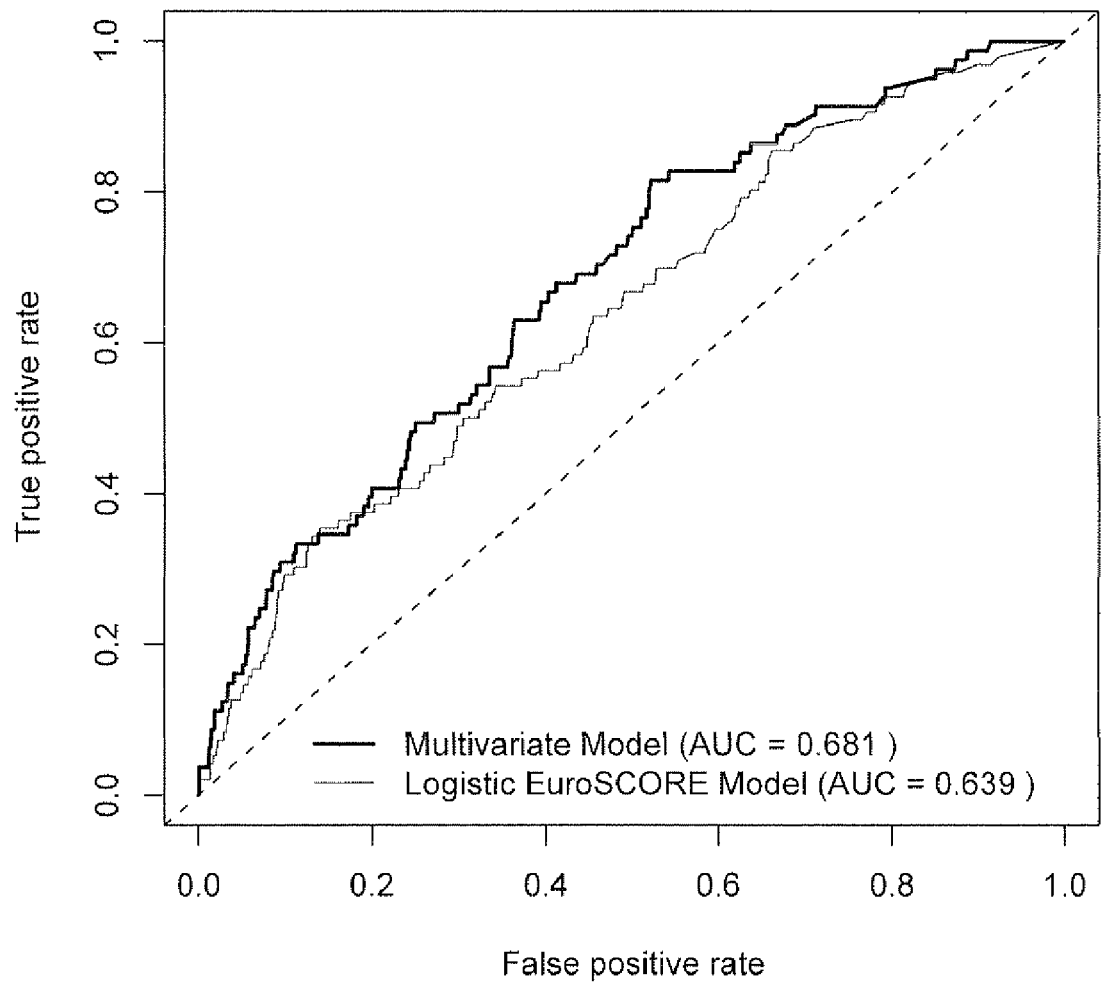
Figure 6: Receiver Operator Characteristic (ROC) Curves of Logistic EuroSCORE and Clinico-genomic Models

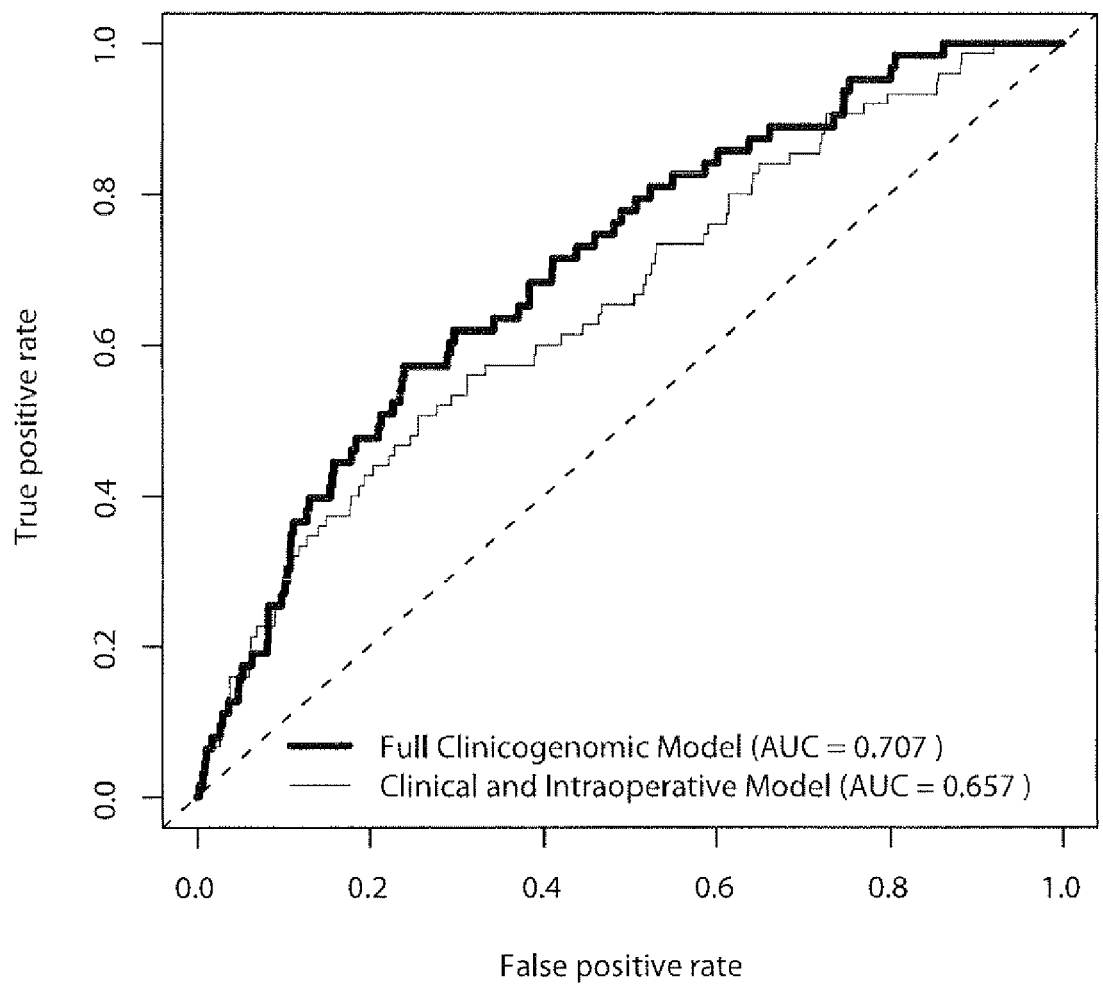
Figure 7: Receiver Operator Characteristic (ROC) Curves of Logistic EuroSCORE and Combined Clinico-genomic Models

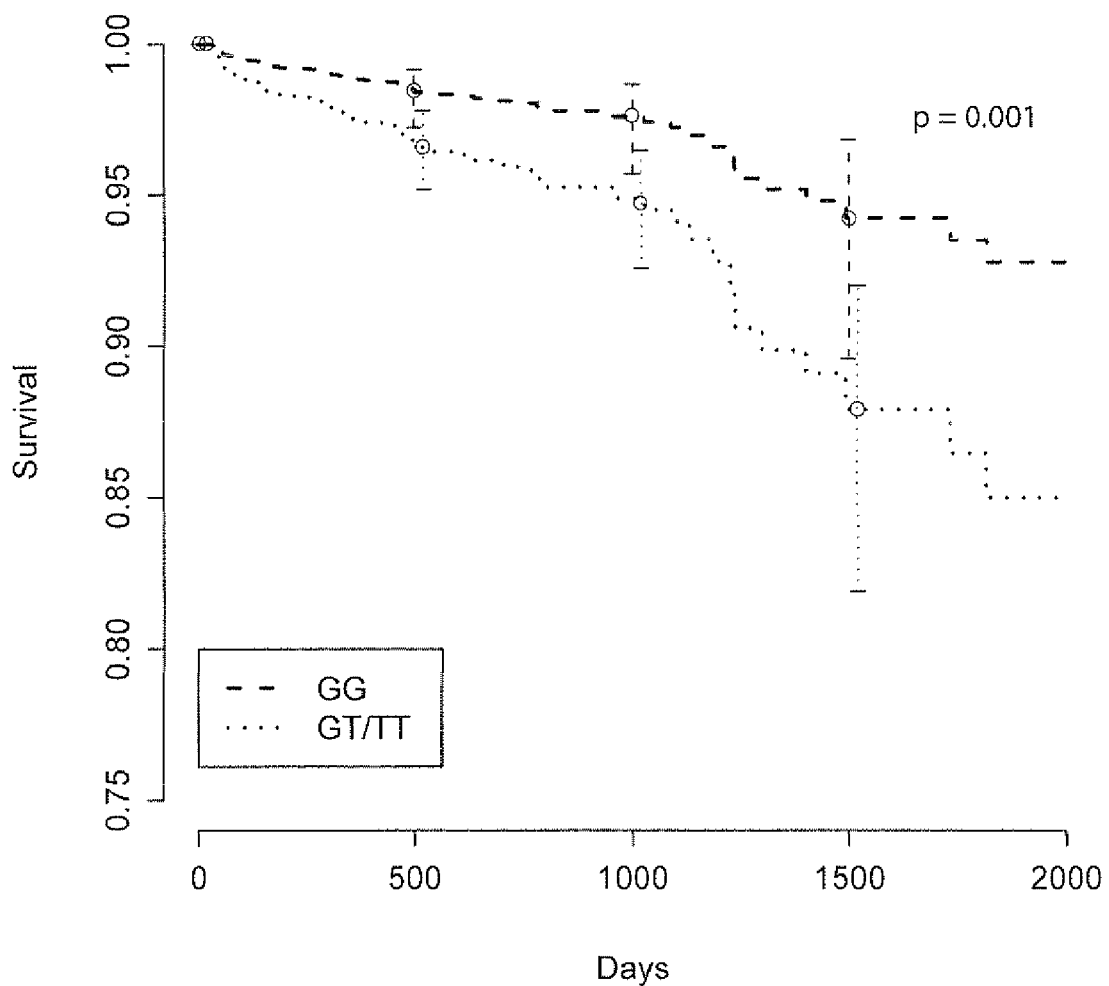
Figure 8: Long-term survival by APOE genotype (adjusted for baseline EuroSCORE, Aprotinin use, and CPB duration)

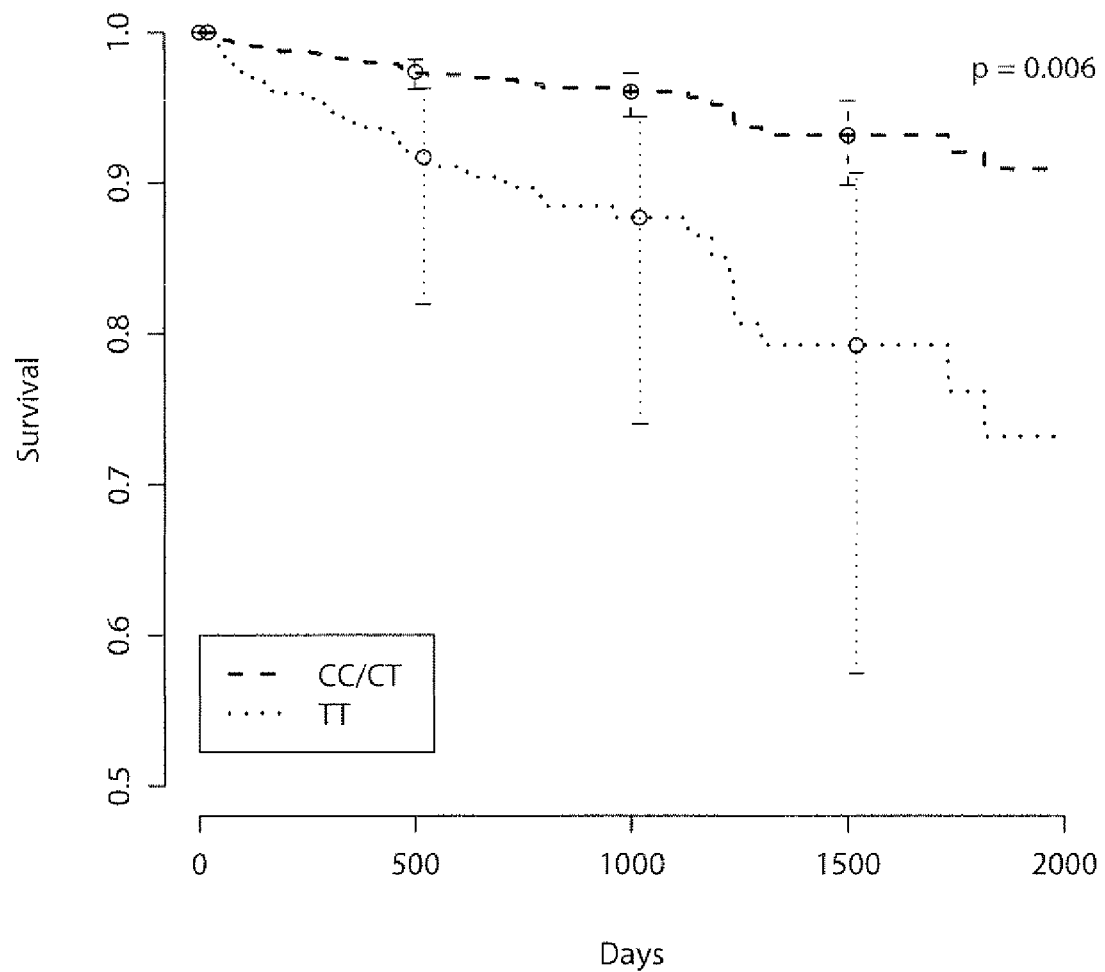
Figure 9: Long-term survival by THBD genotype (adjusted for baseline EuroSCORE, Aprotinin use, and CPB duration)

PREDICTORS OF LONG-TERM MORTALITY FOLLOWING CORONARY ARTERY BYPASS GRAFT SURGERY

This application claims priority from U.S. Provisional Application No. 60/960,763, filed Oct. 12, 2007, the entire content of which is incorporated herein by reference.

TECHNICAL FIELD

The present invention relates to methods of identifying individuals at increased risk of mortality following coronary artery bypass graft (CABG) surgery and to compositions and kits suitable for use in such methods.

BACKGROUND

Several models have been developed to estimate the risk of mortality following cardiac surgery, including the European System for Cardiac Operative Risk Evaluation (EuroSCORE) (Roques, Eur. J. Cardiothorac. Surg. 15:816 (1999)). These models are limited, however, in their ability to predict death for specific individuals. It has been hypothesized that individual gene polymorphisms can improve the discriminatory ability of EuroSCORE with respect to long-term mortality following coronary artery bypass graft (CABG) surgery (Nilsson, Eur. Heart J. 27:768 (2006)). The present invention results, at least in part, from studies designed to identify genetic polymorphisms associated with altered five-year mortality risk following CABG surgery.

SUMMARY OF THE INVENTION

The present invention relates generally to methods of identifying individuals at risk of perioperative mortality and to compositions and kits suitable for use in such methods.

Objects and advantages of the present invention will be clear from the description that follows.

BRIEF DESCRIPTION OF THE DRAWINGS

FIG. 1: Cox Proportional Hazard Model of EuroSCORE-adjusted Survival by Genotype.

FIG. 2: ROC Analysis of EuroSCORE and Clinico-genetic Models.

FIG. 3: Baseline Kaplan-Meier Survival by EuroSCORE Category.

FIG. 4: Kaplan-Meier Survival for RS405509 Dominant Genotype Model.

FIG. 5: Kaplan-Meier Survival for RS1042579 Recessive Genotype Model.

FIG. 6: Receiver Operator Characteristic (ROC) Curves of Logistic EuroSCORE and Combined Clinico-genomic Models.

FIG. 7: Receiver Operator Characteristic (ROC) curves for the Clinicogenomic and Clinical Covariate Models.

FIG. 8: Long-term survival by APOE genotype (adjusted for baseline EuroSCORE, Aprotinin use, and CPU duration).

FIG. 9: Long-term survival by THBD genotype (adjusted for baseline EuroSCORE, Aprotinin use, and CPB duration).

DETAILED DESCRIPTION OF THE INVENTION

The present invention results from studies designed to examine the association between specific genetic polymorphisms and mortality risk after surgery (e.g., cardiac surgery). These studies demonstrate that specific genetic variants are associated with an increased risk of postoperative mortality. It will be appreciated from a reading of this disclosure that polymorphisms in apolipoprotein E (APOE) and thrombomodulin (THBD) are independently associated with altered five year mortality risk following, for example, CABG surgery.

Biological effects for the single nucleotide polymorphisms (SNPs) referenced above, and described in greater detail in the Examples that follows, have been demonstrated. APOE −219T reduces transcriptional activity of the gene through differential binding of nuclear proteins (Artiga, FEBS Lett 421:105-8 (1998)), reduces plasma APOE concentrations in a dose-dependent manner and was associated with increased risk of MI independent of the presence of other SNPs including APOE ε2/ε3/ε4 (Lambert, Hum Mol Gen 9(1):57-61 (2000)). THBD 455Val SNP, located in the sixth EGF-like domain responsible for thrombin binding and activation of protein C, was previously associated with increased risk of CAD and MI (Wu, Circulation 103:1386 (2001)).

The present invention provides definitive association between these genetic variants and postoperative mortality risk. The invention is exemplified by reference to cardiac surgery patients but includes all perioperative, periprocedure (endoscopy, bronchoscopy, cardiac catheterization, angioplasty, etc.), and intensive care unit settings.

The presence of one or more of the above-referenced polymorphisms present in a sample (e.g., a biological sample such as blood) can be determined using any accurate detection method, including a variety of genotyping techniques known in the art (e.g., using a preoperative "CHIP" or SNP panel). Examples of such techniques include the use of polymerase chain reaction and extension primers (see too the Example below). Suitable techniques also include the use of RFLP analysis and mass spectrometry (see also Ye et al, Hum. Mutat. 17(4):305 (2001), Chen et al, Genome Res. 10:549 (2000)).

The genetic variants (SNPs) described above and in the Examples can be used, for example, to predict postoperative and ICU mortality risk. As indicated above, screening for genetic variants of the invention is also relevant for other invasive procedures including but not limited to endoscopy, bronchoscopy, cardiac catheterization, and angioplasty. Preoperative screening for genetic variants enables clinicians to better stratify a given patient for therapeutic intervention, either with drug therapy or with other modalities. Additionally, knowledge of genetic variants allows patients to choose, in a more informed way in consultation with their physician, medical versus procedural therapy. Identifying these genetic variants in patients who decide to undergo surgery or other invasive procedure enables health care providers to design altered therapeutic strategies aimed at minimizing the incidence of mortality in the subset of patients with enhanced risk.

As indicated above, preoperative genotype testing can refine risk stratification and improve patient outcome. Based on the genetic risk factors identified, treatment regimens, including drug treatment regimens, used to minimize the risk of mortality can be useful in acute settings, for example, cardiac surgery. Identification of the genetic markers described herein can facilitate individually tailored medical therapy (personalized medicine) designed to reduce mortality risk.

The invention also relates to kits suitable for use in testing for the presence of the polymorphisms identified herein. Such kits can include, for example, reagents (e.g., probes or primers) necessary to identify the presence of one or more of the above-referenced polymorphisms.

In a further embodiment, the present invention relates to methods of identifying compounds suitable for use in minimizing the risk of mortality.

Certain aspects of the invention are described in greater detail in the non-limiting Example below, which example can be summarized as follows.

In a prospective cohort of 2071 patients undergoing CABG with cardiopulmonary bypass at a single institution between 1994-2002, a panel of 96 single nucleotide polymorphisms (SNPs) in 52 candidate genes was genotyped by mass spectrometry. All-cause mortality was ascertained through the National Death Index. Long-term mortality was defined as death occurring more than 30 days and less than 5 years after CABG. Chi-squared tests performed on each SNP using three different inheritance models (dominant, recessive, additive) were adjusted for multiple comparisons by permutation analysis. SNPs with permutation-adjusted p-values <0.05 were entered into logistic regression models to adjust for traditional clinical and procedural risk factors (logistic EuroSCORE). Significant covariate-adjusted SNPs (p<0.05) were included in a final clinico-genetic multivariate logistic regression model, Cox proportional hazard ratios were also calculated to determine the effect of each SNP on survival times after adjusting for EuroSCORE. The areas under the receiver operator characteristic curves (C-statistic) were calculated for the clinico-genetic and the EuroSCORE models.

Mortality data were available for 2018 patients (97%) and genotypic information for 1822 patients (88%). Of the 96 candidate SNPs examined, 3 had permutation-adjusted p-values <0.05. The dominant effect of apolipoprotein E (APOE −219G/T) and the recessive effect of thrombomodulin (THBD 1418C/T) SNPs remained significant after covariate adjustment in multivariate modeling (Table 1, FIG. 1). The associated hazard ratios (95% CIs) were 0.459 (0.265, 0.796) and 2.64 (1.213, 5.745), for APO E and THBD, respectively. Addition of genetic information improved model discrimination based on EuroSCORE only (C-statistic 0.68 versus 0.63, respectively) (FIG. 2). (See also FIGS. 3-6.)

TABLE 1

SNPs Associated with Altered Long-Term Mortality

| SNP | Permutation-adjusted p-value | Covariate-adjusted p-value | Clinico-genetic model p-value | Hazard Ratio (95% CI) |
| --- | --- | --- | --- | --- |
| APOE-219G/T (rs405509) | 0.016 | 0.005 | 0.010 | 0.46 (0.27, 0.79) |
| THBD 1418C/T (Ala455Val) (rs1042579) | 0.028 | 0.0006 | 0.016 | 2.64 (1.21, 5.75) |

In conclusion, common functional polymorphisms in APOE and THBD are independently associated with altered 5-year mortality following CABG surgery and improve predictive models based on traditional risk factors alone.

EXAMPLE

Experimental Details

Patient Population

DNA from a prospective cohort of 2071 patients undergoing CABG with CPB between 1994 and 2002 was examined. All patients were enrolled in the Perioperative Genetics and Safety Outcomes Study (PEGASUS), an Institutional Review Board-approved, prospective, longitudinal study at Duke University Medical Center. Exclusion criteria for the study included history of renal failure, active liver disease, bleeding disorders, autoimmune diseases, or immunosuppressive therapy. A standardized isoflurane/fentanyl anesthetic was administered to all patients. Cold blood cardioplegia and nonpulsatile CPB (30° C. to 32° C.) with a crystalloid prime and pump flow rates >2.4 L/min per m$^2$ was used. α-stat blood gas management, serial hematocrits >=0.18 while on CPB, and activated clotting times >450 seconds were standardized as well.

Patient Mortality

Follow-up was conducted six months after hospital discharge, and annually thereafter by the Duke Clinical Research Institute. All-cause mortality was verified through the National Death Index. For the purposes of this analysis, long-term mortality was defined as all-cause death occurring more than 30 days and less than 5 years following CABG surgery.

Candidates Gene and Polymorphism Selection

Fifty-two candidate genes involved in coronary artery disease, inflammation, and myocardial ischemia-reperfusion injury were selected a priori based on previous publications (Podgoreanu et al, J. Thorac. Cardiovasc. Surg. 130(2):330-339 (2005), Ruel et al, J. Thorac. Cardiovase. Surg. 126(5): 1521-1530 (2003), Ng et al, Nucleic Acids Res. 31(5):3812-3814 (2003), Tomic et al, Circulation 112(19):2912-2920 (2005)) and expert opinion. Ninety-six single nucleotide polymorphisms (SNPs) were selected in these candidate genes with an emphasis on functionally important variants.

Genotype Analysis

Genotyping was performed by matrix-assisted laser desorption/ionization time-of-flight mass spectrometry on a Sequenom system (Sequenom, San Diego, Calif.) at a core facility (Agencourt Bioscience Corporation, Beverly Mass.). Primers used and polymorphism details can be found at anesthesia.duhs.duke.edu/pegasus/. Genotyping accuracy was validated at >99% by scoring a panel of 6 SNPs in 100 randomly selected patients using an ABI 3700 capillary sequencer (Applied Biosystems, Foster City, Calif.).

Statistical Analysis

Prior to the inclusion of genetic polymorphisms in the analysis, a multivariate logistic regression model was constructed to estimate perioperative mortality risk using traditional clinical and intraoperative risk factors (clinical covariate model). The logistic EuroSCORE (Nashef et al, Eur. J. Cardiothorac. Surg. 16(1):9-13 (1999), Michel et al, Eur. J. Cardiothorac. Surg. 23(5):684-687 (2003), Nashef et al, Eur. J. Cardiothorac. Surg. 22(1):101-105 (2002)) was calculated for each patient to summarize preoperative and procedural factors that increase perioperative mortality. Additional demographic and intraoperative variables were added to the logistic regression equation using forward selection.

A two-stage analysis strategy was used for polymorphism selection (Hoh et al, Ann. Hum. Genet. 64(Pt 5):413-417 (2000)). Allelic associations with long-term mortality were first assessed using $\chi^2$ tests for each polymorphism. The association tests were performed using additive (homozygote major allele versus heterozygote versus homozygote minor allele), dominant (homozygote major allele versus heterozygote plus homozygote minor allele), and recessive (homozygote minor allele versus heterozygote plus homozygote major allele) models for each polymorphism to avoid assumptions regarding inheritance modes. Because of the number of comparisons performed, permutation testing was used to adjust p-values at this step (Good, Permutation tests: a practical guide to resampling methods for testing hypotheses, 2$^{nd}$ edn. New York: Sprinter; (2000)). Polymorphisms with permutation-adjusted p-values <0.05 were retained for further analysis. Next, multivariable logistic regression was used to test the association between mortality and individual SNPs while adjusting for baseline perioperative risk factors, which were determined in constructing the clinical covariate model. SNPs were added to the logisitic regressing model using forward selection to produce a clinicogenomic model. Both main effects and interactions between SNPs were allowed. Age and sex are included in the logistic EuroSCORE and, as a result, were not included in the stepwise variable selection. Self-reported ethnicity was also tested as a covariate in the logisitic regression model. To assess the discriminative ability of the two completed models, the area under the receiver operator characteristic curves (C-static) was computed for the both the clincical covariate and the clinicogenomic models.

In addition to analyzing mortality with logistic regression, Cox proportional hazard models were constructed to take advantage of time-to-event information within the dataset. Variables from the completed clinicogenomic model were included in the Cox proportional hazard regression model to compute covariate-adjusted hazard ratios for the SNPs of interest.

Results

Mortality data were available for 2018 patients (97%) and genotypic information for 1822 patients (88%). Baseline demographics of the study population can be seen in Table 2. Of the traditional clinical and procedural variables, forward variable selection resulted in two statistically significant independent predictors of long-term mortality (Table 3). Intraoperative aprotinin use, which was statistically significant in univariate analyses, lost statistical significance in full clinical covariate model. Self-reported ethnicity was not a statistically significant predictor of mortality in either univariate or multivariate models.

TABLE 2

Baseline Demographic, Clinical and Procedural Characteristics

| Characteristic | N | Survived N = 1725 | Died N = 96 | P-value |
|---|---|---|---|---|
| LOGEUROSC | 1821 | 1.78 3.10 6.31 (5.68 ± 7.33) | 2.52 5.12 13.57 (10.00 ± 12.5) | <0.001[1] |
| AGE | 1821 | 55.80 64.00 71.50 (63.19 ± 10.74) | 61.08 69.40 76.00 (68.10 ± 9.83) | <0.001[1] |
| PUMPTIME | 1816 | 89.0 111.0 134.0 (112.9 ± 45.8) | 98.0 120.0 153.5 (130.4 ± 52.2) | 0.002[1] |
| SEX: 2 | 1818 | 71% $\frac{1215}{1722}$ | 67% $\frac{64}{96}$ | 0.417[2] |
| APROT | 1619 | 9% $\frac{132}{1544}$ | 17% $\frac{13}{75}$ | 0.009[2] |
| RACETXT: Asian | 1361 | 0% $\frac{4}{1280}$ | 0% $\frac{0}{81}$ | 0.741[2] |
| African American | | 8% $\frac{103}{1280}$ | 7% $\frac{6}{81}$ | |
| Native American | | 2% $\frac{30}{1280}$ | 1% $\frac{1}{81}$ | |
| Other | | 1% $\frac{7}{1280}$ | 0% $\frac{0}{81}$ | |
| Unknown | | 20% $\frac{253}{1280}$ | 15% $\frac{12}{81}$ | |
| Caucasian | | 69% $\frac{883}{1280}$ | 77% $\frac{62}{81}$ | |
| RS405509: G | 1562 | 34% $\frac{506}{1475}$ | 20% $\frac{17}{87}$ | 0.017[2] |
| GT | | 43% $\frac{637}{1475}$ | 52% $\frac{45}{87}$ | |
| T | | 23% $\frac{332}{1475}$ | 29% $\frac{25}{87}$ | |
| RS1042579: C | 1665 | 69% $\frac{1095}{1576}$ | 63% $\frac{56}{89}$ | 0.005[2] |
| CT | | 27% $\frac{427}{1576}$ | 27% $\frac{24}{89}$ | |
| T | | 3% $\frac{54}{1576}$ | 10% $\frac{9}{89}$ | |

$_a b_c$ represent the lower quartile a, the median b, and the upper quartile c for continuous variables. x ± s represents $\bar{X} \pm 1$ SD.
N is the number of non-missing values.
Tests used: [1]Wilcoxon test; [2]Pearson test

TABLE 3

Statistically Significant Preoperative and Intraoperative Variables

|  | Estimate | Std. Error | z value | Pr(>|z|) |
|---|---|---|---|---|
| (Intercept) | -4.30192 | 0.34521 | -12.46168 | 0.00000 |
| I(log(LOGEUROSC)) | 0.47240 | 0.12329 | 3.83167 | 0.00013 |
| APROT1 | 0.30996 | 0.34080 | 0.90950 | 0.36309 |
| PUMPTIME | 0.00420 | 0.00214 | 2.00774 | 0.04467 |

|  | Low | High | Δ | Effect | S.E. | Lower 0.95 | Upper 0.95 |
|---|---|---|---|---|---|---|---|
| LOGEUROSC | 1.78 | 6.39 | 4.6 | 0.60 | 0.16 | 0.29 | 0.91 |
| Odds Ratio | 1.78 | 6.39 | 4.6 | 1.83 |  | 1.34 | 2.49 |
| PUMPTIME | 89.00 | 135.00 | 46.0 | 0.20 | 0.10 | 0.00 | 0.39 |
| Odds Ratio | 89.00 | 135.00 | 46.0 | 1.22 |  | 1.00 | 1.48 |
| APROT - 1:0 | 1.00 | 2.00 |  | 0.31 | 0.34 | -0.36 | 0.98 |
| Odds Ratio | 1.00 | 2.00 |  | 1.36 |  | 0.70 | 2.66 |

Of the 96 candidate SNPs examined, three had permutation-adjusted p-values <0.05. After forward variable selection and adjustment for baseline logistic EuroSCORE and duration of cardiopulmonary bypass, the dominant model main effects of the −219G>T polymorphism in apolipoprotein E (RS405509) and the recessive model main effect of the Ala455Val polymorphism in thrombomodulin (RS1042579) remained statistically significant independent predictors of long-term mortality in the logistic regression analysis. The resulting odds ratio and 95% confidence interval for APOE −219G>T and THBD Ala455Val were 1.89 (1.01, 3.57) and 2.79 (1.04, 7.52), respectively. The C-statistic for the final clinicogenomic model was 0.707, compared with 0.657 for the clinical covariate model, suggesting improved discriminatory accuracy (FIG. 7).

Survival analyses by APOE and THBD genotype are displayed in FIGS. 8 and 9. The resulting independent hazard ratios (95% confidence intervals) for long-term survival, adjusted for baseline logistic EuroSCORE and cardiopulmonary bypass duration, are 1.96 (1.06, 3.70) and 2.63 (1.04, 6.62) for the polymorphisms within APOE and THBD, respectively. (See also Table 4.)

TABLE 4

Single Nucleotide Polymorphisms (SNP) Associated with Altered Long-Term Mortality

| SNP | Permutation-adjusted p-value | Covariate-adjusted p-value | Clinicogenomic Model p-value |
|---|---|---|---|
| R5405509 (APOE) | 0.016 | 0.020 | 0.048 |
| RS1042579 (THBD) | 0.028 | 0.006 | 0.042 |

While several models have been developed to estimate mortality risk following cardiac surgery, they are limited in their ability to predict death for specific individuals. From a prospective cohort of patients undergoing CABG with CPB, two genetic polymorphisms were found to be associated with altered long-term mortality. These genes may represent new targets for therapies aimed at reducing long-term mortality after CABG surgery. Furthermore addition of genetic information resulted in improved discriminatory ability of the predictive model, providing better information for patients and providers evaluating the risks and benefits of CABG surgery.

Apolipoprotein E plays a critical role in lipid metabolism and in the pathogenesis of atherosclerosis. The −219G>T polymorphisms lies within the regulatory region of the APOE gene and affects circulating plasma apolipoprotein E levels through differential binding of nuclear proteins (Artiga et al, FEBS Lett. 421(2):105-108 (1998)). A previous multicenter study demonstrated an increased risk of myocardial infarction in patients with the −219G>T polymorphism and reported a dose-dependent decrease in apolipoprotein E plasma concentrations according to −219G>T genotype, independent of apolipoprotein isoform (ϵ2/ϵ3/ϵ4) (Lambert et al, Hum. Mol. Genet. 9(1):57-61 (2000)). The results from the present study reinforce the importance of the functional role of apolipoprotein E in cardiovascular pathophysiology.

Thrombomodulin is a an endothelial-specific type I membrane receptor that binds thrombin and alters it so that it changes from a prothrombotic to an antithrombotic enzyme. Thrombomodulin also activates protein C, resulting in inactivation of factor Va and factor VIII. RS1042579 is a nonsynonymous polymorphism that results in an alanine (A) to valine (V) substitution at amino acid positions 455. A recent study demonstrated an association between the Ala455Val substitution and the development of coronary artery disease (Wu et al, Circulation 103(10):1386-1389 (2001)). The findings of the present study provide further support for the participation of thrombomodulin in the development of cardiovascular events.

All documents and other information sources cited above are hereby incorporated in their entirety by reference.

What is claimed is:

1. A method of identifying a human patient with an increased risk of mortality following coronary artery bypass graft (CABG) surgery comprising, obtaining a DNA sample from said human patient, assaying said DNA sample for a polymorphism that results in an alanine to valine substitution at amino acid position 455 of thrombomodulin (THBD), and identifying said human patient as having an increased risk of mortality following CABG surgery when said human patient is homozygous for valine at amino acid position 455 of THBD.

2. A method of identifying a human patient with an increased risk of mortality following coronary artery bypass graft (CABG) surgery comprising, obtaining a DNA sample from said human patient, assaying said DNA sample for a polymorphism that results in an alanine to valine substitution at amino acid position 455 of thrombomodulin (THBD), and identifying said human patient as having an increased risk of mortality following CABG surgery when said human patient is homozygous for valine at amino acid position 455 of THBD in comparison to a human patient that is homozygous for alanine at position 455 of THBD or heterozygous for alanine and valine at position 455 of THBD.

* * * * *